(12) United States Patent
Moores et al.

(10) Patent No.: US 9,198,414 B2
(45) Date of Patent: *Dec. 1, 2015

(54) COMPOSITIONS AND METHODS FOR PREVENTING OR REDUCING RESISTANCE OF INSECTS TO INSECTICIDES

(71) Applicants: Rothamsted Research Limited, Harpenden (GB); Department of Primary Industries for and on behalf of the State of New South Wales, Orange (AU)

(72) Inventors: Graham David Moores, Stevenage (GB); Robin Vera Gunning, Tamworth (AU)

(73) Assignees: ROTHAMSTED RESEARCH LIMITED, Harpenden (GB); DEPARTMENT OF PRIMARY INDUSTRIES FOR AND ON BEHALF OF THE STATES OF NEW SOUTH WALES, Orange (AU)

(*) Notice: Subject to any disclaimer, the term of this patent is extended or adjusted under 35 U.S.C. 154(b) by 0 days.

This patent is subject to a terminal disclaimer.

(21) Appl. No.: 13/926,940

(22) Filed: Jun. 25, 2013

(65) Prior Publication Data

US 2013/0287831 A1  Oct. 31, 2013

Related U.S. Application Data

(63) Continuation of application No. 10/512,911, filed as application No. PCT/GB03/01861 on Apr. 29, 2003, now Pat. No. 9,005,641.

(30) Foreign Application Priority Data

Apr. 29, 2002 (GB) .................................. 0209749.1

(51) Int. Cl.
*A01N 25/00* (2006.01)
*A01N 25/28* (2006.01)
(Continued)

(52) U.S. Cl.
CPC ................ *A01N 25/34* (2013.01); *A01N 25/00* (2013.01); *A01N 25/28* (2013.01); *A01N 43/30* (2013.01); *A01N 53/00* (2013.01)

(58) Field of Classification Search
CPC ....... A01N 25/00; A01N 25/28; A01N 25/34; A01N 43/30; A01N 53/00
USPC .......................................... 424/405, 408, 451
See application file for complete search history.

(56) References Cited

U.S. PATENT DOCUMENTS

| 4,497,793 A | 2/1985 | Simkin |
| 5,194,264 A | 3/1993 | Van Tonder |
| 5,516,674 A | 5/1996 | Roe et al. |

FOREIGN PATENT DOCUMENTS

| DE | 2411373 | * | 9/1975 | ............. A01N 17/00 |
| DE | 19515186 | | 4/1995 | |

(Continued)

OTHER PUBLICATIONS

Gunning et al., Esterase Inhibitors Synergize the Toxicity of Pyrethroids in Australian *Helicoverpa armigera* (Hubner) (Leptidoptera: Noctuidae), 1999; Pesticide Biochemistry and Physiology, 63:50-62.*

(Continued)

*Primary Examiner* — Jane C Oswecki
(74) *Attorney, Agent, or Firm* — Nixon Peabody LLP

(57) ABSTRACT

A method for preventing or reducing resistance to a pesticide of a substrate pest, which method comprises the administration to the substrate or the pest of a composition comprising: (a) a rapid-release formulation of an inhibitor of a factor causing or contributing to the resistance of the pest to the pesticide; and, substantially simultaneously, (b) a non-rapid release formulation of the pesticide. The invention also provides compositions suitable for use in such a method.

10 Claims, 7 Drawing Sheets

(51) Int. Cl.
*A01N 25/34* (2006.01)
*A01N 43/30* (2006.01)
*A01N 53/00* (2006.01)

(56) References Cited

FOREIGN PATENT DOCUMENTS

| EP | 0427991 | 9/1997 |
|---|---|---|
| EP | 0830813 A1 | 3/1998 |
| GB | 1513614 | 6/1978 |
| WO | WO 00/02557 | 1/2000 |

OTHER PUBLICATIONS

Gunning et al., Inhibition of Resistance-related Esterases by Piperonyl Butoxide in *Helicoverpa armigera* (Lepidoptera: Noctuidae) and *Aphis gossypii* (Hemiptera: Aphididae); Academic Press, 1998, pp. 215-225.*
Syngenta data sheet (http://www.syngenta.com/en/products_brands/karate_page.html), (Aug. 21, 2009).
Results for experiments 1 and 2, which compare a composition comprising PBO and encapsulated pesticide with pretreatment using PBO (filled during examination procedure), (Feb. 2004; Mar. 2007).
Declaration from Dr. Denis Wright (filed during examination procedure), (Sep. 14, 2006).
Nauen, R., Assoc. Ed., Pest Management Science, forwarding referree's comments on Bingham et al. article, (Aug. 14, 2006).
The Patent Office (UK); Examination Report on GB0309773.0, mailed, (May 25, 2004).
Gunning et al., "Inhibition of Resistance-related Esterases by Piperonyl Butoxide in *Helicoverpa armigera* (Lepidoptera: Noctuidae) and *Aphis gossypii* (Hemiptera: Aphididae)", Academic Press, 1998, 215-225.
Syngenta data sheet (http://www.syngenta.com/en/products_brands/karate_page.html), (downloaded Aug. 19, 2009).
Results for experiments 1 and 2, which compare a composition comprising PBO and encapsulated pesticide with pretreatment using PBO (filled during examination procedure), Oct. 4, 2007.
Declaration from Dr. Denis Wright (filed during examination procedure), Sep. 14, 2006.
Results for experiments 3 and 4, which illustrate the efficacy of administering a composition comprising PBO and encapsulated pesticide to treat resistant pest populations, Feb. 2008.
Cole et al., "Influence of monooxygenase inhibitors . . . ", Plant Science, 1987, 50:13-20.
Powles et al., "Herbicide cross resistance . . . ", Herbicide Resistance Action Committee, 2007, www.plantprotection.org.
Kotze et al., "Synergism of rotenone by piperonyl butoxide . . . ", Veterinary Parasitology, 2006, 136:275-282.
Kotze, "Cytochome P450 monoxygenase activity . . . ", Int. J. Parasitology, 1997, 27(1):33-40.
Kwon et al., "Response of a chlorsulfuron-resistant biotype . . . ", Weed Science, 1995, 43:561-565.
Kwon et al., "The effect of piperonyl butoxide and adjuvants . . . ", Weed Technology, 1996, 10:127-133.
McKellar et al., "Fenbendazole pharmakinetics . . . ", Drug Metabolism and Disposition, 2002, 30:1230-1239.
Sanchez Bruni et al., "Changes to oxfendazole chiral kinetics . . . ", Equine Vet. J., 2005, 37(3) 257-262.
Siranidou et al., "Chemical control of *Fusarium* . . . ", J. Plant Diseases and Protection, 2001, 108(3):231-243.
Varsano et al., "Mode of action of piperonyl butoxide . . . ", Pesticide Biochem. Physiology, 1992, 44:174-182.
Gunning, R. et al., "Esterase inhibitors synergize the toxicity of pyrethroids in Australian *Helicoverpa armigera* (Hubner) (Lepidoptera: Nocturidae)", Pestic Biochem Physiol., 1999, 63:50-62.
Canadian Patent Office, action mailed Apr. 4, 2008, in respect of application 2,484,904.
European Patent Office, action mailed Sep. 2, 2008, in respect of Notice of Opposition to EP 1499183.
Bingham et al., "Temporal synergism by microencapsulation . . . ", Pest Manag Sci, 2007, 63:276-281.
Nauen, R., Assoc. Ed., Pest Management Science, forwarding referree's comments on Bingham et al. article, Oct. 4, 2007.
The Patent Office (UK); Examination Report on GB0309773.0, mailed May 25, 2004.
The Patent Office (UK); Examination Report on GB0309773.0, mailed Sep. 19, 2003.
The European Patent Office; Examination Report on EP03 730 310.4, mailed Apr. 4, 2007.
The European Patent Office; Examination Report on EP03 730 310.4, mailed Mar. 27, 2006.

\* cited by examiner

COMPOSITIONS AND METHODS FOR PREVENTING OR REDUCING RESISTANCE OF INSECTS TO INSECTICIDES

The present invention relates to a method for preventing or reducing resistance of a pest to a pesticide and to formulations for use in such a method. In particular, the invention relates to insecticide resistance and to insecticidal compositions.

There are several definitions of insecticide resistance, often reflecting the interest of the scientist attempting the definition, rather than the phenomenon itself. The World Health Organisation has defined resistance as "the development of an ability in a strain of insects to tolerate doses of toxicant that would prove lethal to the majority of individuals in a normal population of the same species". Pesticide resistance is therefore to be similarly construed, although the main pests addressed herein are insects.

Insecticide resistance has become progressively more widespread since first being scientifically recorded in 1914. Over 500 insect and mite species now show tolerance to pesticides, and pesticide resistance has become a serious threat to the future success of pest control using chemicals.

There are three major mechanisms by which resistance can occur: reduced penetration of the pest by the pesticide; metabolism of the insecticide (resulting in detoxification); and target-site insensitivity. These resistance mechanisms may exist individually in an insect, but are often found in combination where the overall resistance offered is substantially higher; this situation is referred to as 'multi-factorial resistance'.

Many insects possess detoxification systems, which evolved originally to protect the insect from natural toxins in the environment. Metabolism of the insecticide may occur before it reaches its target-site when it comes into contact with those detoxifying enzymes that render it either less toxic or more easily excreted, or both. The most important enzyme systems involved in insecticide resistance include the groups a) mixed function oxidases, b) glutathione S-transferases and c) esterases. Resistance resulting from enhanced activity of one or more of these enzyme groups has been found in several insect species.

Insect detoxifying enzyme systems can be studied either in vivo by conventional bioassays, or in vitro by biochemical assays. In conventional bioassays, there is widespread employment of synergists such as DEF (S,S,S-tributyl phosphorothioate) and TPP (O,O,O-triphenyl phosphate). These are compounds that significantly enhance the toxicity of an insecticide, although they may be virtually non-toxic when used alone. Insecticide synergists act by inhibiting metabolic enzymes. Mortality differences in a bioassay, using a pesticide in the presence or absence of a synergist, should indicate whether a putative metabolic enzyme is involved in resistance. However, caution should be taken when using synergists; very often the chemical is not completely specific to the enzyme being examined, and it may be difficult to assess its possible effect upon other biological systems.

Esterases are enzymes that catalyse the hydrolysis of an ester bond. Organophosphate, carbamate and most pyrethroid insecticides contain ester bonds and in some instances are sensitive to hydrolysis by esterases.

Esterases can act by either sequestering toxins to the insect or by hydrolysing the toxins. Therefore resistance to insecticides can result from either quantitative or qualitative changes in carboxylesterases, or a combination of the two. Qualitative changes could confer to the enzyme the ability to hydrolyse insecticidal esters at a significant rate, but may or may not affect the activity of the esterase towards the model substrates. Without a qualitative change, resistance can still occur by quantitative changes resulting from a process of gene amplification. This leads to the production of a greater amount of the same esterase, which sequesters the insecticide, resulting in resistance. Occasionally, the esterase may be both altered and amplified.

Piperonyl butoxide (PB or PBO) has been used extensively as a 'tank mix', both as an excipient due to its detergent/surfactant properties, and because of the wealth of literature describing its ability to inhibit oxidative metabolic enzymes (mixed function oxidases). We have shown that certain non-specific esterases involved in pesticide resistance are partially inhibited by micromolar concentrations of piperonyl butoxide (IUPAC, London 1998).

In Australian *Helicoverpa armigera* (Hübner), up to 70% of the activity of pyrethroid-resistance related esterases was inhibited by $10^{-5}$ M piperonyl butoxide, both in homogenates of resistant insects and in a partially-purified esterase extract (Gunning et al in Piperonyl Butoxide, pp 215-25, Academic Press (1998)).

Studies were also performed on esterases from the cotton aphid, *Aphis gossypii* (Glover) and the peach-potato aphid, *Myzus persicae* (Sulzer). Piperonyl butoxide was capable of inhibiting esterase activity from *A. gossypii*, but only when present at nominal concentrations of $10^{-4}$ M or greater. Total esterase activity was typically reduced by 50% in 30 minutes. This effect is not simply a consequence of a physico-chemical effect involving the substrate, since esterases present in *M. persicae* directly implicated in insecticide resistance were not inhibited when incubated with mM concentrations of piperonyl butoxide for 40 minutes.

Gunning et al (1998) therefore proposed the use of a synergist or esterase inhibitor such as PBO simultaneously in a tank mix with an insecticide such as pyrethroid to improve efficacy of the insecticide in the field. Furthermore, data obtained by Gunning et al (Pest Biochem & Physiol 63 50-62 (1999)) reveal significant pyrethroid synergism by organophosphates; in earlier studies, workers in the field did not observe this effect, doubtless because the pre-treatment period used in such studies (profenofos and DEF) never exceeded 30 minutes, which is too short a period for such an effect to become evident.

Thus, in some cases where resistance is conferred by esteratic enzymes, PBO or similarly acting analogue of PBO, such as a UV stable variant thereof, could be added to inhibit the esterases for a period of time prior to the addition of a conventional insecticide. This would normally necessitate a second insecticide application, ie a pre-treatment with a metabolic enzyme inhibitor prior to insecticide spray, which is not an economic proposition compared to a single application e.g. of the tank mix.

The present invention overcomes the problem of multiple application by proposing that, if an insecticide were microencapsulated or otherwise administered in a non-immediate release formulation and the PBO or other esterase inhibitor not so, then a single application would suffice. The PBO would immediately begin to act on the esterases and, after a given period, the micro-encapsulation would break down and release the conventional insecticide. By this time, the resistance-associated enzymes would be inhibited, and thus the resistance mechanism overcome.

Various formulations involving both a synergist, such as PBO, and an insecticide, such as a pyrethroid are known.

European patent specification no. 238 184 relates to the use of a microencapsulated pesticide and a non-micro-encapsulated pesticide, wherein the two pesticides are preferably the same, eg permethrin. European patent specification no. 427

991 discloses a mixture of a microencapsulated organophosphorous and/or carbamate pesticide with a flowable phase comprising a pyrethroid pesticide. Both of these specifications suggest the use of the formulation for kill-knock down combined action, as does the German patent specification no. 2411 373, which discloses a partly micro encapsulated formulation of a pyrethroid, optionally containing a synergist. The entire text of all three of these earlier patent applications is hereby incorporated by reference. However, none of these formulations relates to one suitable for the purposes of this invention, namely to reduce or prevent pesticide resistance by enabling an esterase inhibitor to come into contact with the pest first, followed by the pesticide, in a single application.

Accordingly, the present invention provides a method for preventing or reducing resistance to a pesticide by a pest, which method comprises the administration to the crop, other substrate or the pest of a composition comprising:
(a) a rapid-release formulation of an inhibitor of a factor causing or contributing to the resistance of the pest to the pesticide; and, substantially simultaneously,
(b) a non-rapid-release formulation of the pesticide.

Furthermore, the present invention provides a composition, suitable for use in such a method, which composition comprises:
(a) a rapid-release formulation of an inhibitor of a factor causing or contributing to the resistance of the pest to the pesticide; and, substantially simultaneously,
(b) a non-rapid-release formulation of the pesticide.

Preferably, the rapid release formulation and the sustained release formulation are comprised in the composition in physical admixture. However, the formulations (a) and (b) may be administered separately. By 'substantially simultaneously' herein is meant that the formulations are brought into contact with the substrate and/or the pest at about the same time, avoiding the need to revisit the site of the substrate and/or pest in order to apply the second of the two formulations. Both formulations would thereby come into contact with the substrate and/or the pest within the order of seconds, preferably within 10 seconds and more preferably, within one or two seconds, of each other rather than in the order of minutes or longer. Preferably, the formulations (a) and (b) are administered simultaneously.

The rapid release formulation is suitably any standard pesticide formulation known to those skilled in the art and suitable for the purpose. Such formulations include, for example, wettable powders, granulates, emulsifiable concentrates and ultra-low volume formulations to which water can be added to form an emulsion, a suspension and the like. Preferably, the rapid release formulation, comprising PBO or other metabolic enzyme inhibitor, is in the form of an emulsifiable concentrate. It will be appreciated that the preferred enzyme inhibitor, or combination of enzyme inhibitors, will be selected on the basis of which pesticide compound or compounds are being employed against a specific pest.

The non-rapid release formulation is suitably any non-immediate release formulation known in the art, such as sustained, controlled or slow release formulations suitable for the purpose. Preferably, the non-rapid release formulation is one that prevents an effective dose of the pesticide from being released or coming into effective contact with the pest or its target in the pest until the esterase inhibitor, or inhibitor of another factor causing or contributing to pesticide resistance, has at least begun its inhibiting effect on its target in the pest. Suitably, the non-rapid release formulation prevents release of the pesticide or contact thereof with the pest or the substrate for at least 30 minutes after application of the composition. Such formulations include, for example, the pesticide encapsulated in a degradable capsule and preferably comprise micro-encapsulation technology. One such example of a surface spray encapsulating a pyrethroid insecticide is Karate Zeon [trademark] (lambda-cyhalothrin). The optimal time delay for release of the pesticide will be determined by a number of factors and will require experimentation to determine the time/response profile of the inhibitor(s) selected. A non-release formulation which corresponds with this profile will then be selected/developed.

Suitable micro-encapsulation formulations include those analogous to those described in the aforementioned European and German patent specifications but adapted so as to microencapsulate the insecticide (eg pyrethroid) and not the metabolic enzyme inhibitor (eg esterase inhibitor, eg PBO).

The pesticide itself is suitably any that is capable of acting as such and to which resistance has been identified amongst the or some of the pest(s) against which it is otherwise active. Examples of suitable pesticides that may comprise the active ingredients of component (b) of the composition therefore include pyrethroids, organo-phosphates and carbamates. Preferably, the pesticide is a pyrethroid, such as fenvalerate, s-fenvalerate, cypermethrin (both alpha and zeta forms), bifenthrin, deltamethin and beta-cyfluthrin. It will be appreciated that new pesticides and new classes of pesticides are discovered from time to time, and that resistance to pesticides can develop over time. It is intended that the principles of this invention, and the inventive concepts therein, can be applied to a wide range of pesticides, both known and those yet to be discovered, as and when resistance is identified.

Component (b) therefore preferably comprises an amount equivalent to a standard dosage of the pesticide. For example, in the case of beta-cyfluthrin for pesticidal activity against *Helicoverpa*, a typical dose comprises 8 g/L of an ultra-low volume or 25 g/L of an emulsifiable formulation; and for alpha-cypermethrin a typical dose comprises 16 g/L of an ultra-low volume or 100 g/L of an emulsifiable formulation.

The inhibitor is suitably any that is capable of preventing or reducing resistance of the pest(s) to the pesticide. Suitable inhibitors therefore include esterase inhibitors, microsomal oxidase inhibitors and glutathione S-transferase inhibitors. Preferably, the inhibitor is an esterase inhibitor, such as PBO, ethion, profenofos and dimethoate.

Component (a) preferably comprises an amount of the inhibitor sufficient to prevent or reduce the resistance of the pest(s) to the pesticide and will depend on pest size (eg a white fly needs a lot less inhibitor than an *H. armigera* grub), degree of ester-mediated resistance etc, but is determinable by those skilled in the art.

The pest(s) against which the composition of the invention is/are directed can be any which are known to offer at least some resistance to a pesticide and which it is considered necessary to disable and/or kill. Examples include those that attack or damage or otherwise reduce the commercial or other value of a substrate, such as crops, particularly arable crops, such as food and material crops including cotton. Other pests include those that are a nuisance to or an adversary of other living organisms, including mammals, such as humans.

Accordingly, the pest(s) may include one or more of *Helicoverpa armigera, Helicoverpa punctigera, Heliothis virescens, Aphis gossypii, Myzus persicae, P. includens, W. cervinata, Bemisia tabaci* and mosquito species.

By way of example, the cotton bollworm *Helicoverpa armigera* and B-biotype *B. tabaci* (Poinsettia or silverleaf whitefly) are major crop pests worldwide. Extreme insecticide resistance exacerbates the pest status of these insects. Pyrethroid and Other resistances in Australian *H. armigera* and B-biotype *B. tabaci* are caused by an over production of esterase isoenzymes which sequester and metabolise insecticides.

For administration to the substrate, any method known in the art for application of a pesticide or the like to a substrate may be used and may depend upon factors such as the particular substrate (eg crop), target pest stage of the crop and the like. Examples of such methods include spraying by ground or aerial application. For administration to crops, particularly over vast areas such as the Australian cotton fields, it is preferred to spray a composition comprising a suspension or emulsion of the components (a) and (b) in water, optionally also comprising a surfactant or other excipients, (although PBO itself can act as a surfactant) or an ultra-low volume (omitting the water) composition, supplied in a tank, such as one adapted to be transported by aircraft or, for example as in the case of whitefly sprays, by ground rig (such as tractor, tank or boom spray).

The rate of administration of the compositions according to the invention will accord with known or approved (registered) rates of the active ingredients of each of the formulations (a) and (b). For example, for *H. armigera*, the registered rate in Australia for PBO is in the range of from 250-360 g a.i./ha and for a pyrethroid rates is in the range of from about 12-80 g a.i./ha.

The present invention therefore further provides:
(a) the use of a composition according to the invention in the treatment or prevention of pesticide resistance;
(b) the use of a composition according to the invention in the treatment or prevention of damage to or destruction of a substrate by a pest;
(c) the use of a composition according to the invention in pest control; and
(d) a method for preparing a composition according to the invention, which method comprises bringing the components (a) and (b) into physical admixture.

The present invention will now be illustrated by the following Examples.

BRIEF DESCRIPTION OF THE FIGURES

The invention will now be described, by way of example only, with reference to the following Figures wherein:—

FIG. 1 shows percentage *H. armigera* esterase activity (expressed as % of control, ±standard deviation) remaining at fixed periods following topical application of 10 of 1% PBO;

FIG. 2 shows percentage B-type *B. tabaci* (Australian) esterase activity (expressed as % of control, ±standard deviation) remaining at fixed periods following exposure to 0.1% PBO;

FIGS. 3 & 4 show comparison of percentage esterase inhibition by *H. armigera* larvae using PBO pre-treatment, fenvalerate and zeta-cypermethrin;

EXAMPLES

General Methods & Materials

Figure 5:
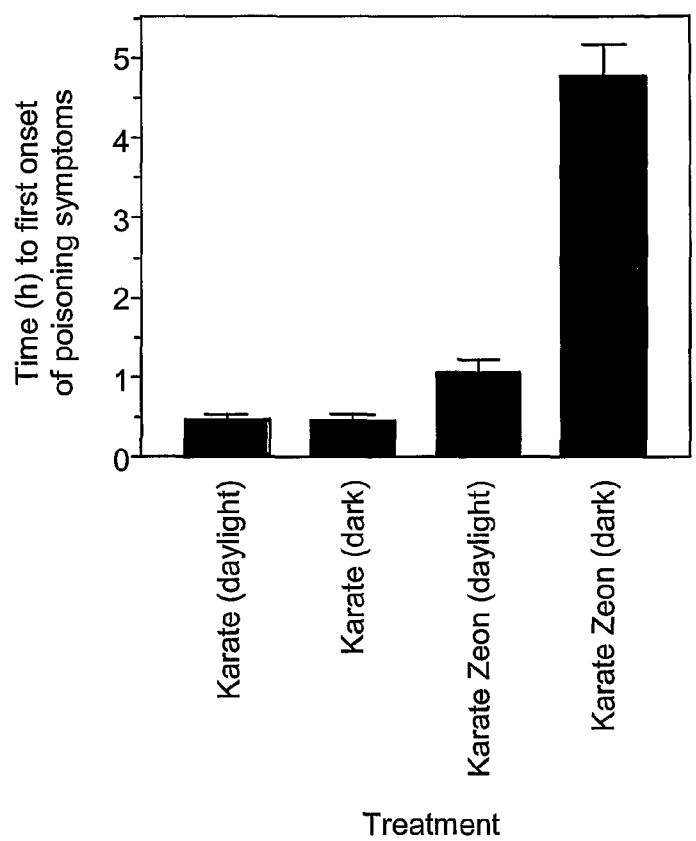
FIG. 5 shows rate of onset of symptoms of pyrethroid poisoning (in daylight and night) in $3^{rd}$ instar pyrethroid susceptible *H. armigera* larvae. Larvae were treated, by topical application, with a discriminating dose of lambdacyhalothrin using either Karate or Karate Zeon.

Esterase activity was determined by measuring the rate of hydrolysis of the model substrate, 1-naphthyl acetate, by carboxylesterases present in organo-phosphate resistant insects such as *H. armigera*, or the hydrolysis of 1-naphthyl buturate for B. tabacii. Such hydrolysis will result in a characteristic yellow/brown colour after complex with FBRR (fast blue RR salt) with absorbance at 450 nm, which is measured to determine the reaction rate. FBRR (0.6% of final solution), was dissolved in pH6.0, 0.2M phosphate buffer (0.5 L), then 1.86% 1-naphthyl acetate or 1-naphthyl butyrate was added.

Kinetic assays were performed using a Bio-Rad 3550 micro plate reader (Bio-Rad Laboratories, UK using Kinetic Collector 2.0 software run on a Mackintosh SE micro-computer), taking absorbance readings at 450 nm automatically at 14-second intervals for 10 minutes. The rate was calculated by the online computer as the slope of the fitted regression line, using an absorbance limit of 2.0; readings are given in milli-OD (unit of optical density).

Insecticides used were technical grade: fenvalerate (98%, Shell) (R—(R*,S*))-4-chloro-α(1-methylethyl)benzene acetic acid, cyano (3-phenoxyphenyl) methyl ester); cypermethrin ((R,S)-alpha-cyano-3-phenoxybenzyl-(1RS)-cis, trans-3-(2,2-dichloro-vinyl)-S,S-dimethylcyclopropane-carboxylate); and zeta-cypermethrin ((S)-cyano(3-phenoxyphenyl)-methyl(±)-cis-trans-3-(2,2,-dichloroethenyl)-2,2-dimethylcyclo-propanecarboxylate) (85%, FMC). The insecticide synergist, piperonyl butoxide (96% pure, technical grade), and an 800 g/l emulsifiable concentrate formulation of this chemical (PBEC80) were supplied by Endura Spa, Bologna, Italy.

Example 1

PBO Inhibits *H. armigera* Esterases

Kinetic assays confirmed that esterase activity was inhibited by the insecticide synergist, PBO, over a 24-hour period (FIG. 1), providing evidence that PBO inhibits *H. armigera* esterases. In addition, kinetic assays illustrate that esterase inhibition by PBO does not occur immediately after dosage, but occurs with maximum enzyme inhibition from 3 to 4 hours after (70 to 72% esterase activity inhibition). Generally, esterases begin to gradually recover until full esterase activity is present at 24 hrs. However, it should be noted that percentage esterase of control remains at less than 50% between 2 and 11 hrs.

Example 2

PBO Inhibits B-Type *B. tabaci* Esterases

Figures 1, 2:
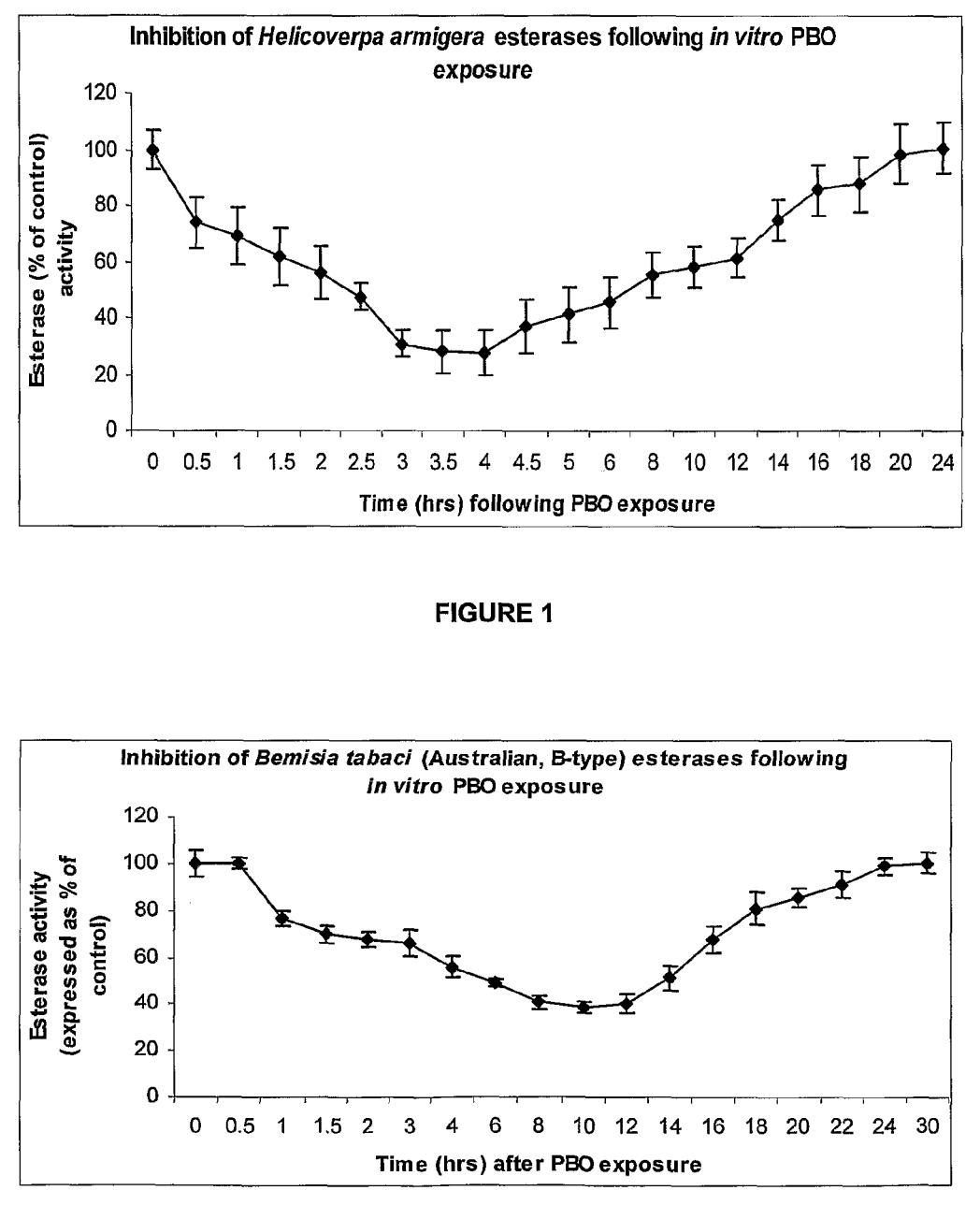

Kinetic assays also showed that PBO inhibits B-type *B. tabaci* esterases over a 26-hour period. After an initial rapid inhibition of esterases (by 1 hour), there is a gradual decrease to maximum esterase inhibition (36% of control at 11 hours), prior to a gradual recovery in esterase activity with full esterase activity witnessed, 30 hours after initial PBO exposure (FIG. 2). Percentage activity of the control remains at less than 50% between 7.5 and 17 hours and, overall, esterases suffer some degree of inhibition between 1 and 26 hours.

Example 3

PBO Increases Pyrethroid Mortality

Figures 3, 4:
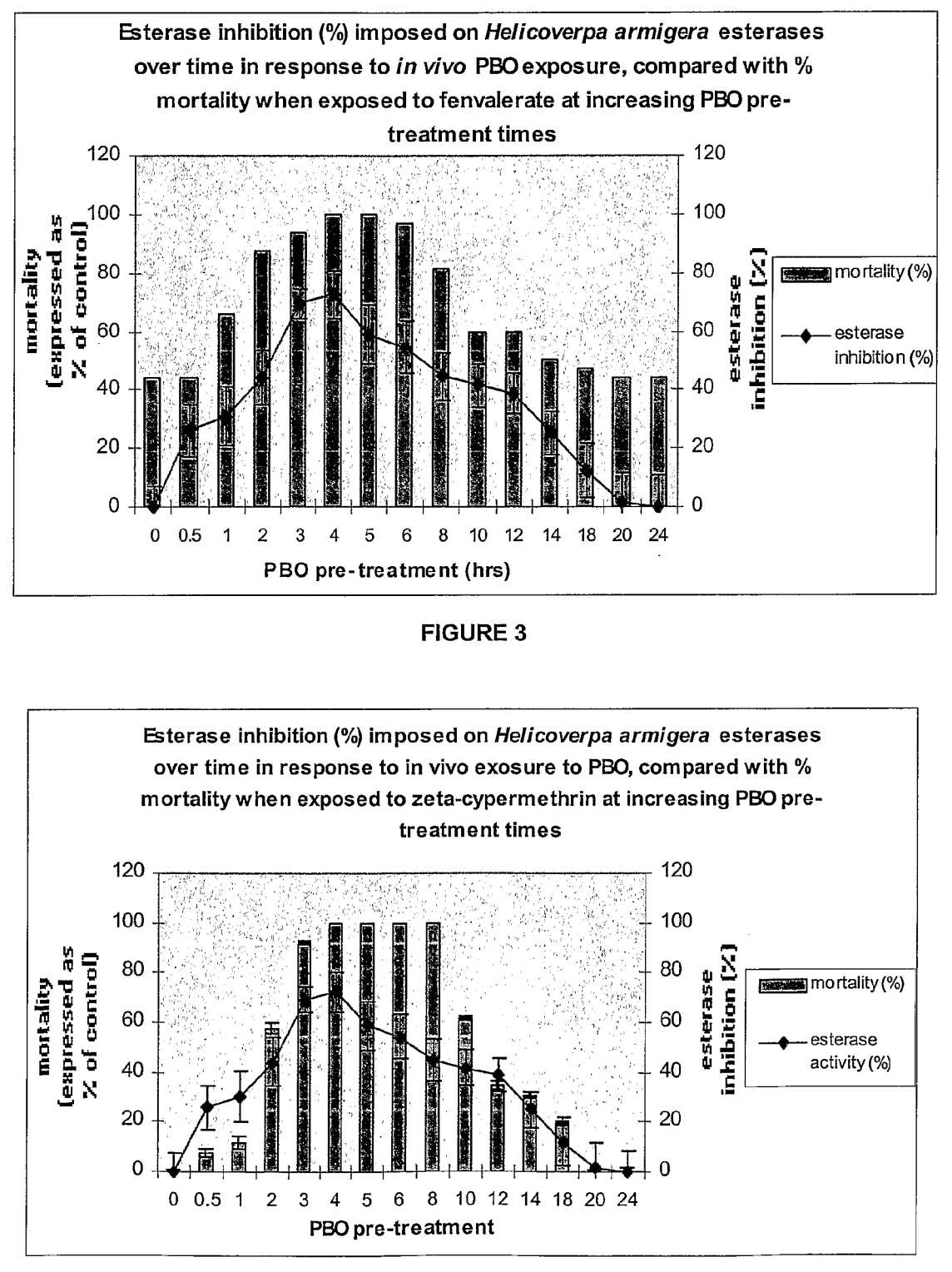

Synergism studies confirmed that PBO increases pyrethroid mortality (FIGS. 3 & 4). These involved a comparison of esterase inhibition (expressed as % of control, ±standard deviation) incurred by *H. armigera* larvae over time following topical application of 1 µl PBO (1%), and the effect on mortality of pyrethroid-resistant larvae when exposed to increasing PBO (1 µl, 1% PBO/larva) pre-treatment intervals before fenvalerate (1 µl, 0.125% fenvalerate/larva, FIG. 3) and zeta-cypermethrin (1 µl, 0.01% zeta-cypermethrin/larva, FIG. 4) exposure. Effects were more pronounced with zeta-cypermethrin. There is a highly significant ($p<0.01$) increase in mortality, until a plateau (100% mortality) is reached (4-5 hrs for fenvalerate, and 4-10 hrs for zeta-cypermehrin); thereafter, the synergistic effects decline. This trend corresponds with earlier findings, where esterases are inhibited to a high degree (more than 50% reduction in esterase activity) between 4 and 18 hours.

Example 4

Composition

The following ingredients may be mixed together in water to form a composition suitable for application from ground or air at standard rates for the pyrethroid:
Formulation (a): 800 g/L PBO (PBO EC formulation)
Formulation (b): 250 g/L Lambda-cyhalothrin (in the form of Karate-Zeon (trademark)); (Karate-Zeon is 250 g/L a.i.)

Example 5

Laboratory Studies with *H. Armiciera*

Introduction
Laboratory bioassays on pyrethroid resistant and susceptible *H. armigera* were conducted in darkness to delay the release of pyrethroid from microencapsulation using Karate Zeon®.
Karate Zeon® is a microencapsulated formulation of the pyrethroid lambdacyhalothrin and is the only encapsulated insecticide on the Australian field crop market. Developed to increase operator safety, this formulation provides a delayed lambdacyhalothrin release (in sunlight after mixing with water), of approximately 30 minutes, Release of the microcapsule contents is partially triggered by sunlight. A 30-minute delay in pyrethroid release is, however, insufficient to allow the maximal synergist action needed for control of resistant insects. Nonetheless, pyrethroid release in Karate Zeon®, can be delayed beyond 30 min by reducing light conditions.

To demonstrate proof of the concept of control of insecticide resistance, using a simultaneous application of a synergist and a delayed release insecticide, we used Karate Zeon® and artificially delayed pyrethroid release from encapsulation by using the insecticide in darkness. However, the technology required to prepare delayed release insecticide formulations with a longer time delay to release is known to those skilled in the art. Thus, microencapsulation techniques may be applied and adapted to give the desired time delay with a specific insecticide.
General Methods
*H. armigera* populations used were: pyrethroid susceptible strain and a pyrethroid selected, resistant strain (approximately 80 fold resistant to lambdacyhalothrin). Third instar pyrethroid resistant and susceptible *H. armigera* larvae were treated with the insecticide synergist piperonyl butoxide (PBO) and two formulations of lambdacyhalthrin Insecticides used were: piperonyl butoxide (800 g/L ai), non-encapsulated Karate EC® (50 g/L ai). microencapsulated Karate Zeon® (250 g/L ai). Insecticides were serially diluted in water. Insecticides were applied topically to larvae, using a standard, *Helicoverpa* bioassay procedure (Gunning et al, 1984). Experiments were conducted at 25° C. Mortality was assesses after 24 h. Control groups were treated with water or PBO and there was no control mortality. Full dosage mortality curves were plotted. Data were analysed by probit analysis.
Proof of Delay of Pyrethroid Release in Darkness
Pyrethroids are neuro-toxins affecting the insect peripheral nervous system and symptoms of poisoning in *H. armigera* are well known Gunning, R.V. (Bioassay for detecting pyrethroid nerve insensitivity in Australian *Helicoverpa armigera*, Journal of Economic Entomology, 89:816-819, 1996). Time of delay of pyrethroid release was estimated (using treatments of Karate EC and Zeon Karate), by recording time to first onset of pyrethroid poisoning symptoms in pyrethroid susceptible *H. armigera*. Larvae were treated with a dose known to kill 100% of susceptible *H. armigera* larvae, both in strong daylight and in darkness. Three replicates of 30 insects were dosed for each treatment. Night observations of larvae were made under red light (insects cannot see red light).
Results (FIG. 5) show that poisoning symptoms developed in *H. armigera* treated with non-encapsulated Karate EC in approximately 30 minutes, both in daylight and darkness. Using encapsulated Karate Zeon, poisoning symptoms developed in approximately one hour in daylight, while dark conditions delayed the onset of poisoning symptoms until 4.5 h. Thus, use of Karate Zeon in darkness delayed pyrethroid release from its microencapsulation by approximately 3.5 h.
Night Bioassays with Pyrethroid Resistant *H. armigera*
Karate EC and Karate Zeon were serially diluted in water to form a range of concentrations for bioassay (0.005-10 µg lambdacyhalothrin/A. Groups of pyrethroid resistant or susceptible larvae (n=30) received the following insecticide treatments under red light and were held in darkness:
Susceptible Strain
Karate EC, Karate Zeon
Resistant Strain
Karate, Karate EC+PBO, Karate Zeon. Karate Zeon+PBO. Each insect received a dose of 10 µg of PBO

TABLE 1

Probit anaysis of response of pyrethroid resistant and susceptible
H. armigera to night bioassays of formulations of
lambdacyhalothrin and piperonyl butoxide

| Treatment | Slope | $LD_{50}$ (μg/larva) | Fiducial limits | Resistance factor |
|---|---|---|---|---|
| Sus. Karate EC | 2.1 | 0.013 | 0.008-0.020 | — |
| Sus. Karate Zeon | 2.2 | 0.014 | 0.008-0.023 | — |
| R. Karate EC | 1.3 | 0.60 | 0.45-0.87 | 46 |
| R. Karate Zeon | 1.3 | 0.60 | 0.45-0.82 | 46 |
| R. Karate EC + PBO | 1.3 | 0.33 | 0.25-0.45 | 25 |
| R. Karate Zeon + PBO | 2.1 | 0.013 | 0.008-0.02 | 1 |

Figure 6:
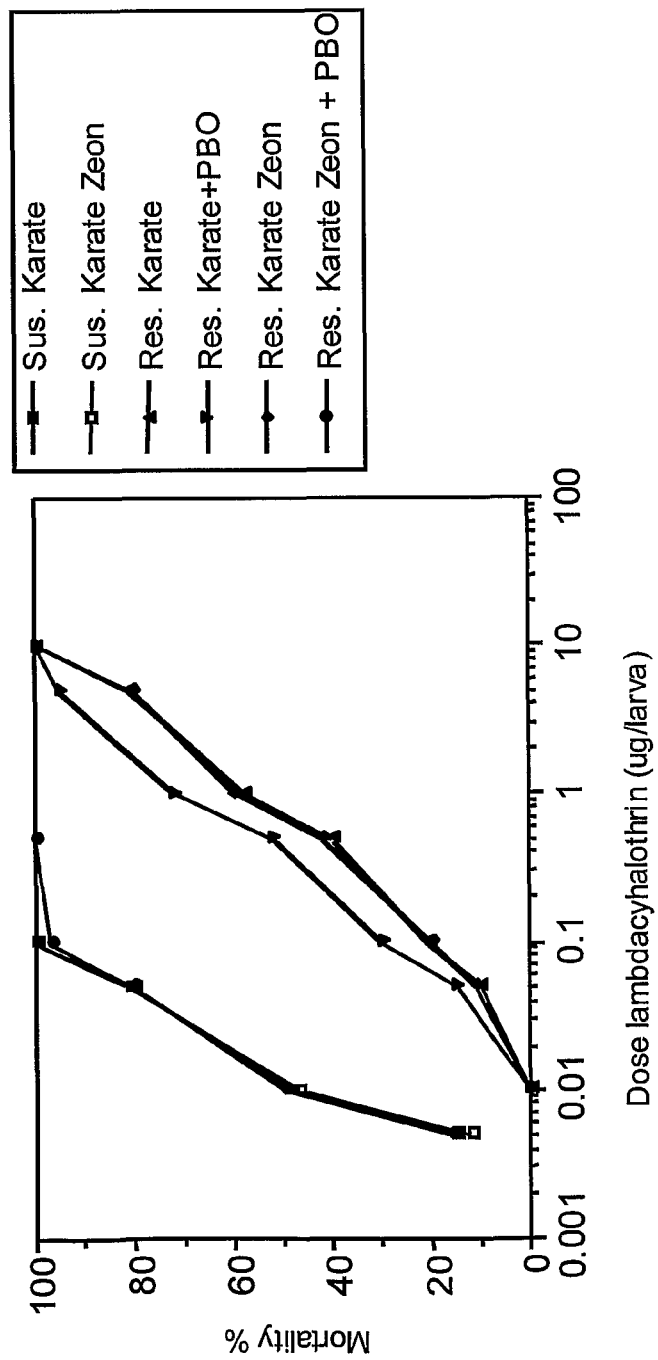
FIG. 6 shows toxicity, using a topical application bioassay, of Karate EC and Karate Zeon and mixtures of piperonyl butoxide (1%) and Karate EC and Karate Zeon to pyrethroid susceptible and resistant (80 fold resistant to lambdacyhalothrin) $3^{rd}$ instar *H. armigera*. Insecticides were applied to *H. armigera* at night (under red light) and bioassays were left overnight in darkness.

Bioassay results are shown in Table 1 and FIG. 6. The toxicities of Karate EC and Karate Zeon to susceptible larvae were not significantly different. Toxicities of Karate EC and Karate Zeon to resistant *H. armigera* were also indistinguishable (46 fold resistance factor). PBO and delayed release Karate Zeon completely overcame resistance (RF=1), while a PBO and Karate EC reduced the level of resistance to 25 fold.

Conclusions

*H. armigera* treated with PBO and delayed release Karate Zeon became effectively susceptible to lambdacyhalothrin with complete suppression of resistance. Night use of Karate EC+PBO incompletely suppressed resistance, further emphasising that, in order to control resistant insects, a delay between PBO application and pyrethroid release is necessary for optimal esterase inhibition by PBO.

Example 6

Laboratory Studies with B-Biotype Bemisla Tabaci

Introduction

Laboratory bioassays on pyrethroid resistant and susceptible B-biotype *B. tabaci* were conducted in darkness to delay the release of pyrethroid from microencapsulation using Karate Zeon®.

General Methods

Pyrethroid susceptible (Northern Australian native *B. tabaci*) and resistant B-biotype *B. tabaci* adults (~2000 resistant fold to lambdacyhalothrin) were treated with formulated insecticide synergist piperonyl butoxide and two formulations of lambdacyhalothrin (non-encapsulated Karate EC® and microencapsulated Karate Zeon®). Insecticides used were piperonyl butoxide 800 g/L EC, Karate EC (50 g/L EC) and Karate Zeon (250 g/L).

Formulated lambdacyhalothrin was serially diluted in water to form a number of test concentrations (0.1-10000 ppm lambdacyhalothrin). A standard leaf dip bioassay technique for adult whiteflies was used (Cahill 1995). Cotton leaf discs were dipped in lambdacyhalothrin concentrations in a mixture containing 1% PBO. The leaves were dried and placed on an agar bed in petri dishes. Adult whiteflies were added and the peri dishes sealed. Bioassays were conducted at night at 25° C. Water dipped and PBO controls were performed. Mortality was assessed and corrected for control mortality (which did not exceed 5%) Full dose response curves were plotted and data analysed by probit analysis.

Results

Figure 7:
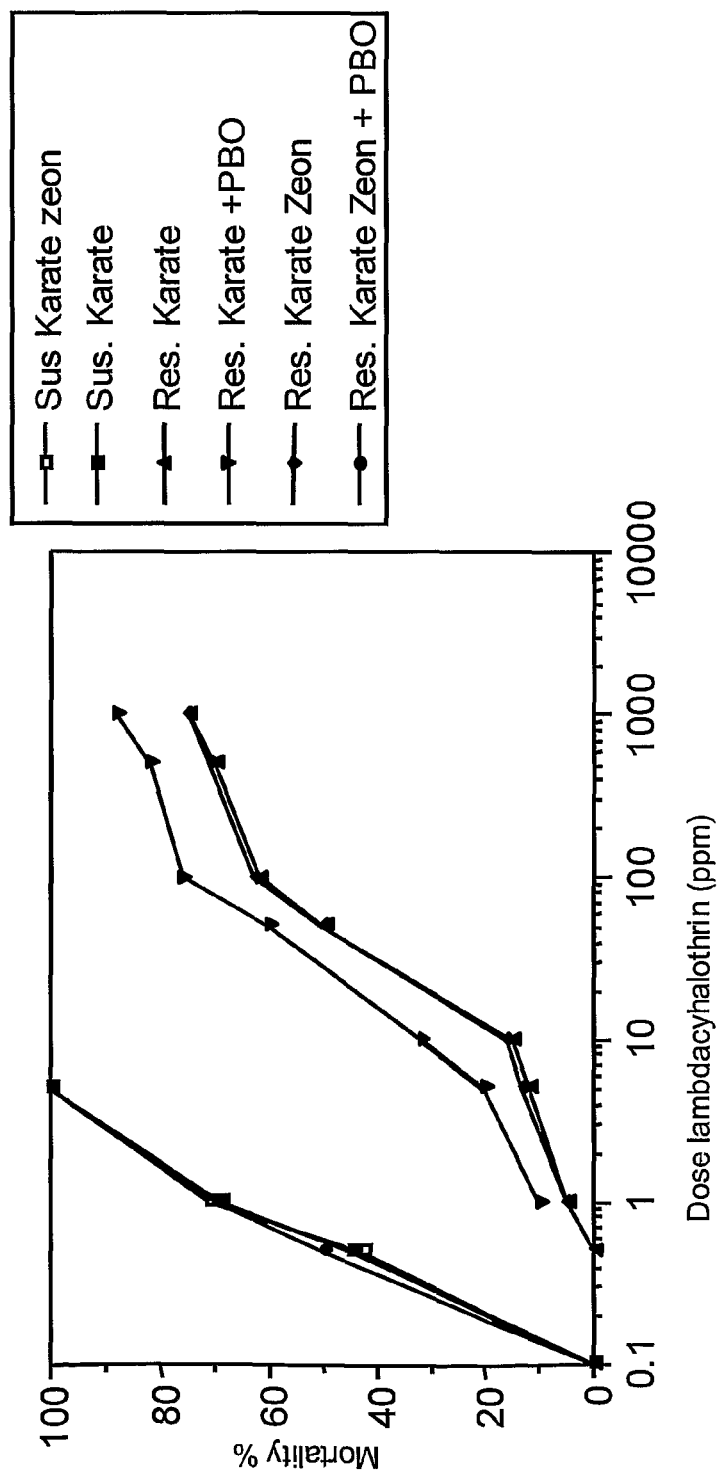
FIG. 7 shows toxicity, using a leaf dip bioassay, of Karate EC and Karate Zeon and mixtures of piperonyl butoxide (1%) and Karate EC and Karate Zeon to adult pyrethroid susceptible native *B. tabaci* and resistant (2000 fold resistant to lambdacyhalothrin) B-biotype *B. tabaci*. Insecticides were applied to *B. tabaci* at night (under red light) and bioassays were left overnight in darkness.

Dosage mortality data are shown in Table 2 and FIG. 7. Data from susceptible *B. tabaci* show no differences between the toxicity of Karate EC and Karate Zeon. There were also no differences between the toxicity of Karate EC and Karate Zeon to resistant *B. tabaci* (RF~140). Pyrethroid resistant *B. tabaci* treated with PBO and delayed release Karate Zeon were indistinguishable from susceptible strains in response to lambdacyhalothrin (RF=1), while treatment with PBO and Karate EC reduced resistance to lambdacyhalothrin somewhat (RF=52).

TABLE 2

Probit analysis of the response of pyrethroid resistant and susceptible
H. armigera to night bioassays of formulations of
lambdacyhalothrin and piperonyl butoxide

| Treatment | slope | $LD_{50}$ (ppm) | Fidicial limits | Resistance factor |
|---|---|---|---|---|
| Sus Karate EC | 3.0 | 0.60 | 0.50-0.73 | — |
| Sus Karate Zeon | 3.0 | 0.61 | 0.48-0.73 | — |
| R. Karate EC | 0.90 | 87.3 | 59-129 | 146 |
| R. Karate Zeon | 0.86 | 81 | 54-122 | 135 |
| R. Karate EC + PBO | 0.89 | 31.1 | 21-46 | 52 |
| R. Karate Zeon + PBO | 2.96 | 0.58 | 0.48-0.70 | 1 |

Conclusions

*B. tabaci* treated with PBO and delayed release Karate Zeon became effectively susceptible to lambdacyhalothrin with complete suppression of resistance. Night use of Karate EC+PBO incompletely suppressed resistance, further emphasising that, in order to control resistant insects, a delay between PBO application pyrethroid release is necessary for optimal esterase inhibition by PBO.

Example 7

Field Studies with a Synergist and Delayed Release Pyrethroid on Cotton Against *H. armigera*—Night Sprays Introduction The *H. armigera* laboratory studies described above were followed up with a small-scale replicated field trial on conventional cotton at the Australian Cotton Research Institute at Narrabri, NSW, February 2003.

Trial Method

In the lack of *H. armigera* pressure on cotton, pyrethroid resistant second instar *H. armigera* larvae, which were the progeny a field strain originating from Queensland, were placed on cotton plant. The strain was 20 fold resistant to lambdacyhalothrin.

Insecticides used were piperonyl butoxide 800 g/L a.i EC, Karate EC (50 g/L EC a.i) and Karate Zeon (250 g/L a.i). Insecticides were mixed with water. Insecticides were sprayed at registered rates on cotton of PBO 320 g a.i./ha, and lambdacyhalthrin 15 g a.i/ha, using a calibrated hand held boom spray Treatments were: an untreated control, PBO control, Karate EC, Karate Zeon and Karate EC and Karate Zeon mixed with PBO.

The trial was conducted on replicated, 1 row×2 m plots. Each plot contained from 13-17 mature cotton plants. There was an unsprayed buffer of two rows between each plot. Just prior to sunset, ten second instar *H. armigera* larvae were placed onto the terminals of each plant in the test plots and the plots sprayed. *H. armigera* numbers per plant were assessed one day after treatment. Temperature ranged from 24-26° C. The mean percentage mortality and standard deviation were calculated for each treatment. There was no mortality in the control.

Results

Figure 8:
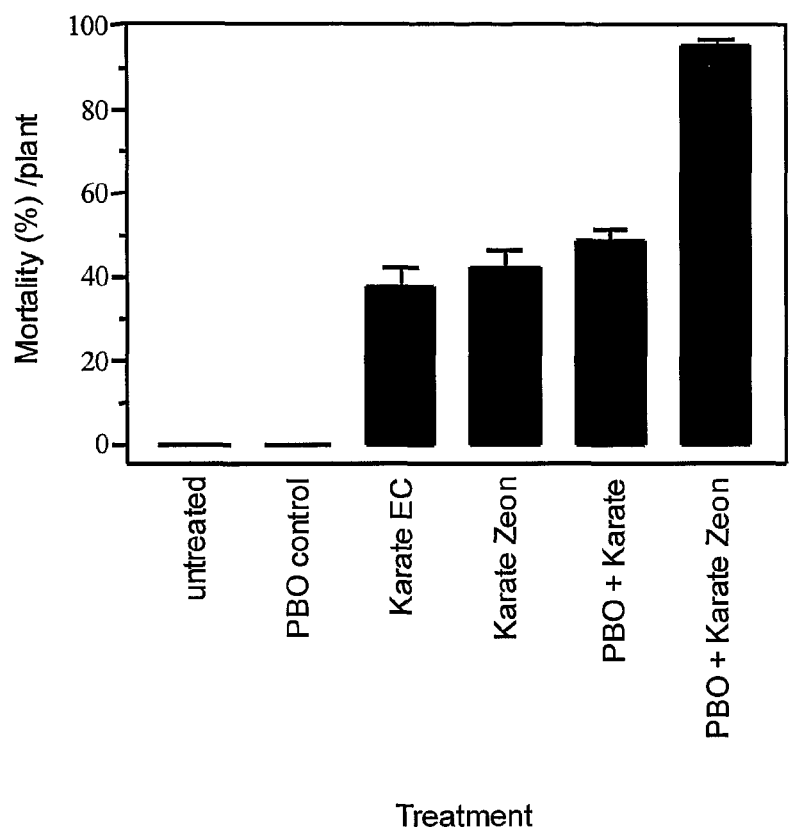
FIG. 8 shows field control on cotton of pyrethroid resistant, second instar *H. armigera* (80 fold to lambdacyhalothrin), using registered rates of delayed release Karate Zeon and immediate release Karate EC, and mixtures of Karate Zeon and Karate EC with PBO. Error bars represent standard deviations. (Rates of insecticide applied were: PBO 320 g a.i./ha, and lambdacyhalothrin 15 g a.i./ha)

Results (FIG. 8) show that lambdacyhalothrin controlled ~40% of *H. armigera* irrespective of formulation, treatment with a PBO+Karate EC mix did not give significantly increase mortality. However, PBO mixed with Karate Zeon gave greater than 90% mortality of resistant insects, indicating almost complete suppression of resistance. These consistent with the results of the laboratory bioassays.

Conclusions

These field data demonstrate that the synergist piperonyl butoxide, when applied simultaneously with a delayed release pyrethroid, provided effective field control of pyrethroid resistant *H. armigera*. Delayed release of pyrethroid allowed time for the synergist to inhibit resistance-associated esterases, providing 100% greater control of pyrethroid resistant *H. armigera* than PBO mixed with a non-encapsulated Karate EC.

Example 8

Field Studies with a Synergist and Delayed Release Pyrethroid on Cotton Against B-Biotype *B. tabaci*—Reduced Light Conditions Introduction The *B. tabaci* laboratory studies described above, were followed up with a small-scale, replicated field trial on conventional, commercial cotton at Emerald, Qld, February 2003. Since rain and high wind prevented any night spraying, insecticides were applied in the morning and the trial conducted under greatly reduced light (heavily overcast, low cloud and rain showers), compared to normal daylight conditions.

Trial Method

The trial was conducted on mature cotton with low *B. tabaci* pressure (~2 whitflies/terminal). Whiteflies were approximately 100 fold resistant to lambdacyhalothrin Insecticides used were piperonyl butoxide 800 g/L a.i EC, Karate EC (50 g/L EC a.i) and Karate Zeon (250 g/L a.i). Insecticides were mixed with water and sprayed at registered rates on cotton (PBO 320 g a.i./ha, and iambdacyhalthrin 15 g a.i/ha) using a calibrated hand held boom spray. Treatments were: an unsprayed control, PBO control, and both Karate EC and Karate Zeon mixed with PBO.

The trial was conducted on replicated, 1 row×10 m plots. There was an unsprayed buffer of two rows between each plot. Whitefly numbers were assessed, by counting adults on each terminal, prior to spraying. The plots were sprayed under reduced ambient light conditions and adult whitefly numbers were assessed one day after treatment. Temperature ranged from 28-34° C. and relative humidity was 80-100%. Mean numbers of whiteflies/terminal and standard deviations were calculated for each treatment.

Results

Figure 9:
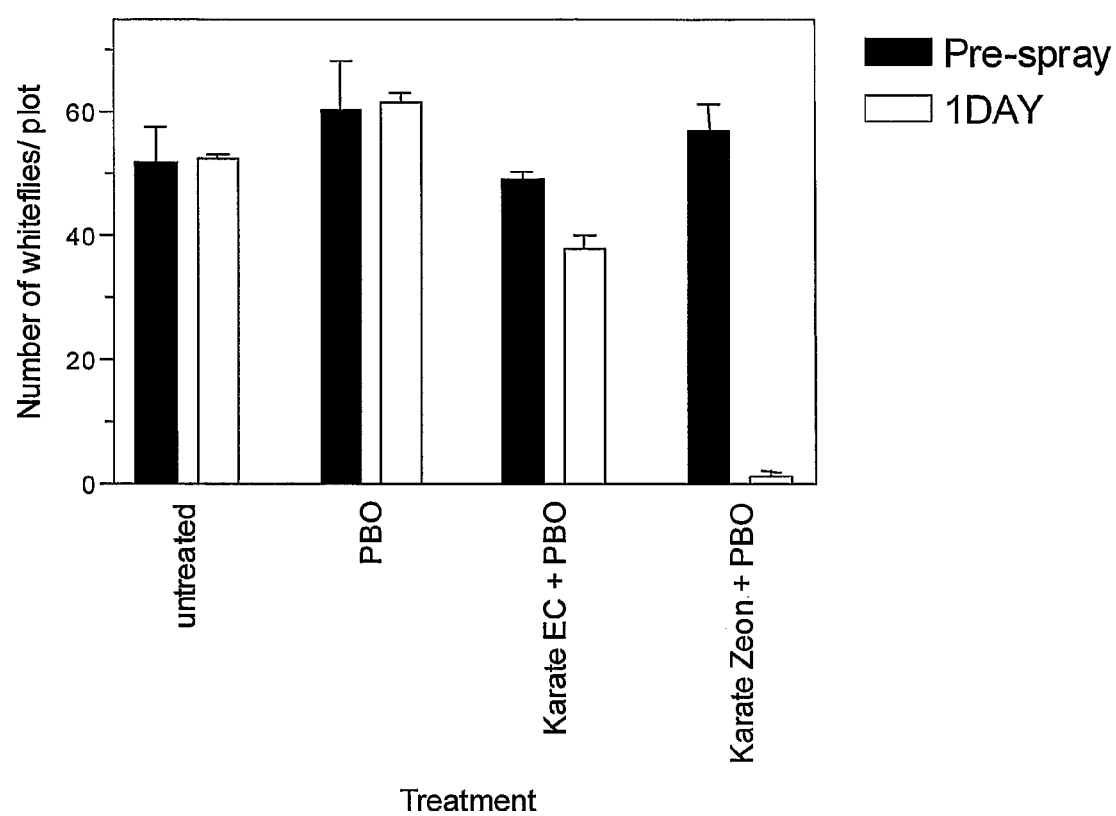
FIG. 9 shows field control on cotton of pyrethroid resistant, B-biotype *B. tabaci* adults, using sprays of registered rates of delayed release Karate Zeon and immediate release Karate EC, and mixtures of Karate Zeon and Karate EC with piperonyl butoxide). Sprays were applied to cotton under heavily overcast light conditions. Error bars represent standard deviations. (Rates of insecticide applied were: PBO 320 g a.i./ha, and lambdacyhalothrin 15 g a.i./ha).

Trial data are shown in FIG. 9. One day after treatment, there was no detectable mortality in untreated, or PBO controls. Differences between whitefly control and lambdacyhalothrin formulation were highly significant. Karate EC mixed with PBO provided some 25% control of whiteflies, while Karate Zeon+PBO gave virtually complete control indicating complete suppression of resistance. Results are consistent with the laboratory bioassay data.

Conclusions

Trial results indicate that very subdued daylight delayed the release of lambdacyhalothrin from encapsulation. There was a sufficient delay between the application of PBO and pyrethroid release from microencapsulation, to allow adequate inhibition of esterases by PBO prior to pyrethroid release. Therefore application of a synergist and a delayed release insecticide controlled highly pyrethroid resistant B-biotype *B. tabaci* in the field.

The invention claimed is:

1. A method for reducing resistance to a pesticide of a substrate pest comprising administering to the substrate or the pest:
   (a) a rapid-release formulation of an esterase inhibitor selected from the group consisting of: S,S,S-tributyl phosphorothionate, 0,0,0-triphenyl phosphate, piperonyl butoxide (PBO), profenofos, ethion, and dimethoate; and substantially simultaneously,
   (b) a pesticide encapsulated in a degradable capsule, thereby reducing resistance of the substrate pest to the pesticide.

2. A method according to claim 1 wherein component (a) and component (b) are administered separately.

3. A method according to claim 2 wherein both components of the composition are administered to the substrate or the pest within 10 seconds of each other.

4. A method according to claim 2 wherein both components are administered to the substrate or the pest within one or two seconds of each other.

5. A method according to claim 1 wherein the inhibitor of component (a) is piperonyl butoxide (PBO).

6. A method according to claim 1 wherein the composition comprises more than one pesticide encapsulated in a degradable capsule.

7. A method according to claim 6 wherein one or more pesticides are microencapsulated within a degradable capsule.

8. A method according to claim 1 wherein the pesticide of component (b) includes at least one compound selected from the group consisting of: pyrethroids; organo-phosphates; and carbamates.

9. A method according to claim 8 wherein the pesticide of component (b) includes at least one pyrethroid selected from the group consisting of: fenvalerate; S-fenvalerate; both alpha and zeta forms of cypermethrin; bifenthrin; deltamethrin; and beta-cyfluthrin.

10. A method according to claim 1 wherein component (a) is piperonyl butoxide and component (b) is a pyrethroid.

* * * * *